US012755819B1

(12) United States Patent
McNair

(10) Patent No.: US 12,755,819 B1
(45) **Date of Patent: *Oct. 6, 2026**

(54) MACROPHAGE ACTIVATION SYNDROMES SEVERITY PREDICTION

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 527 days.

This patent is subject to a terminal disclaimer.

(21) Appl. No.: 15/717,781

(22) Filed: Sep. 27, 2017

Related U.S. Application Data

(60) Provisional application No. 62/403,008, filed on Sep. 30, 2016.

(51) Int. Cl.
*G16H 10/40* (2018.01)
*G16H 10/60* (2018.01)
*G16H 50/50* (2018.01)

(52) U.S. Cl.
CPC ............. *G16H 10/40* (2018.01); *G16H 10/60* (2018.01); *G16H 50/50* (2018.01)

(58) Field of Classification Search
CPC ......... G16H 10/40; G16H 10/60; G16H 50/50
See application file for complete search history.

(56) References Cited

U.S. PATENT DOCUMENTS

2015/0370999 A1* 12/2015 Carpenter .............. G16H 10/60 705/2
2016/0117813 A1* 4/2016 Gross .................... H04W 76/11 600/479

FOREIGN PATENT DOCUMENTS

WO WO-2016007866 A1 * 1/2016 ........... G06F 19/322
WO WO-2016044125 A2 * 3/2016 ........... A61B 5/7435

OTHER PUBLICATIONS

Escobar et al. Piloting electronic medical record-based early detection of inpatient deterioration in community hospitals Journal of Hospital Medicine vol. 11 pp. S18-S24 (Year: 2016).*
Ilapakurti et al. The Role of Big Data in creating Sense EHR, an integrated approach to create next generation mobile Sensor and wearable data driven Electronic Health Record (EHR) 2016 IEEE Second International Conference on Big Data Computing Service and Applications pp. 293-296 (Year: 2016).*
Kumar et al. Automated integration of continuous glucose monitor data in the electronic health record using consumer technology J. Am Med Inform Assoc vol. 23 pp. 523-537 (Year: 2016).*
Wang, William Yang, and Zhenhao Hua. "A semiparametric gaussian copula regression model for predicting financial risks from earnings calls." Proceedings of the 52nd Annual Meeting of the Association for Computational Linguistics (vol. 1: Long Papers). 2014. (Year: 2014).*

(Continued)

*Primary Examiner* — Anna Skibinsky
*Assistant Examiner* — Guozhen Liu
(74) *Attorney, Agent, or Firm* — Mughal Gaudry & Franklin PC

(57) ABSTRACT

Technologies are disclosed for quantitatively predicting whether or not a deterioration in their health status is likely within a future time interval subsequent to computing a prediction. In one embodiment, serial medical data of a particular patient is received from a plurality of inputs. Based on a transformation of the received data, a predicted probability of acute deterioration (PPOD) score is determined. The PPOD score is provided to clinicians, to ensure that timely and effective measures may be taken to mitigate the patient's chances of acute deterioration.

18 Claims, 10 Drawing Sheets

(56) References Cited

OTHER PUBLICATIONS

Madkour, Mohcine, Driss Benhaddou, and Cui Tao. "Temporal data representation, normalization, extraction, and reasoning: A review from clinical domain." Computer methods and programs in biomedicine 128 (2016): 52-68. (Year: 2016).*

* cited by examiner

Copula regression PPOD probability vs. number of lab and physiologic values' threshold transgressions

```
#################################################################################
#
#  HLH copula regression
#
#################################################################################

library(lattice)
library(flexmix)
library(betareg)



library(gcmr)

# load data - y is zero-inflated Poisson count var; x is Gamma or log-normal distributed
continuous var
#          - shock index (HR/SBP) 0.30 to 3.80
hlh_si_transgr <- read.csv(file="c:/0_cerdsm/IP/oncology_HLH/hlh3.csv", header=TRUE,
                    colClasses=c("numeric","integer"))
x <- hlh_si_transgr[,1]           # maxSI
y <- hlh_si_transgr[,2]           # transgr

# fit Gaussian copula regression model with negative binomial marginals
mod1 <- gcmr(y ~ x, data=hlh_si_transgr, marginal=negbin.marg, cormat=ind.cormat())

# show results of copula regression fit
summary(mod1)
# Coefficients marginal model:
#            Estimate Std. Error z value Pr(>|z|)
# (Intercept)  0.73372    0.14986   4.896 9.79e-07 ***
# x            1.83678    0.12685  14.480  < 2e-16 ***
# dispersion   0.23471    0.04224   5.557 2.75e-08 ***
#
# log likelihood = 427.18,  AIC = 860.36

# generate QQ plot of copula regression fit
plot(mod1, 3, col="gray", lwd=2, cex=1.4)

# generate observed-vs-predicted  plot of copula regression fit
plot(mod1, 4, col="gray", lwd=2, cex=1.4)

# fit Gaussian copula regression model with binomial marginals
mod2 <- gcmr(y ~ x, data=hlh_si_transgr, marginal=binomial.marg, cormat=ind.cormat())

# show results of copula regression fit
summary(mod2)
```

*FIG. 6A.*

Model Probabilities Look-up Tables

| TRANSG | MAXSI | Z | SUBSCORE | P | B0 | B1 | B2 | B3 | B4 | B5 |
|---|---|---|---|---|---|---|---|---|---|---|
| 0 | 0.50 | -2.15 | 0.02 | 0.5% | 0.43 | -1.64 | 1.89 | -4.58 | 0.17 | 1.61 |
| 0 | 1.0 | -1.21 | 0.11 | 0.5% | | | | | | |
| 0 | 1.50 | -0.26 | 0.39 | 0.8% | | | | | | |
| 0 | 2.00 | 0.68 | 0.76 | 1.5% | | | | | | |
| 0 | 2.50 | 1.63 | 0.94 | 1.9% | | | | | | |
| 0 | 3.00 | 2.57 | 0.99 | 2.1% | | | | | | |
| 1 | 0.50 | -2.15 | 0.02 | 0.5% | | | | | | |
| 1 | 1.00 | -1.21 | 0.11 | 0.6% | | | | | | |
| 1 | 1.50 | -0.26 | 0.39 | 1.0% | | | | | | |
| 1 | 2.00 | 0.69 | 0.76 | 1.7% | | | | | | |
| 1 | 2.50 | 1.63 | 0.94 | 2.3% | | | | | | |
| 1 | 3.00 | 2.57 | 0.99 | 2.4% | | | | | | |
| 2 | 0.50 | -2.15 | 0.02 | 0.6% | | | | | | |
| 2 | 1.00 | -1.21 | 0.11 | 0.7% | | | | | | |
| 2 | 1.50 | -0.26 | 0.39 | 1.1% | | | | | | |
| 2 | 2.00 | 0.68 | 0.76 | 2.0% | | | | | | |
| 2 | 2.50 | 1.63 | 0.94 | 2.6% | | | | | | |
| 2 | 3.00 | 2.57 | 0.99 | 2.8% | | | | | | |
| 3 | 0.50 | -2.15 | 0.02 | 0.8% | | | | | | |
| 3 | 1.00 | -1.21 | 0.11 | 0.9% | | | | | | |
| 3 | 1.50 | -0.26 | 0.39 | 1.3% | | | | | | |
| 3 | 2.00 | 0.68 | 0.76 | 2.4% | | | | | | |
| 3 | 2.50 | 1.63 | 0.94 | 3.1% | | | | | | |
| 3 | 3.00 | 2.57 | 0.99 | 3.3% | | | | | | |
| 4 | 0.50 | -2.15 | 0.02 | 0.9% | | | | | | |
| 4 | 1.00 | -1.21 | 0.11 | 1.0% | | | | | | |
| 4 | 1.50 | -0.26 | 0.39 | 1.6% | | | | | | |
| ⋮ | ⋮ | ⋮ | ⋮ | ⋮ | | | | | | |

*FIG. 6B.*

MACROPHAGE ACTIVATION SYNDROMES SEVERITY PREDICTION

CROSS-REFERENCE TO RELATED APPLICATION

This application claims priority to U.S. Provisional Patent Application No. 62/403,008, filed Sep. 30, 2016, entitled "Macrophage Activation Syndromes Severity Predication," the entire contents of which are hereby incorporated by reference.

BACKGROUND

Hemophagocytic lymphohistiocytosis (HLH) is a life-threatening syndrome of immune dysregulation and is classified as primary or secondary according to the underlying etiology. Reactive hemophagocytic syndrome is triggered by various infections, hematologic malignancies, and systemic autoimmune diseases (JRA, IM) and is contrasted with familial HLH. The latter condition is associated with mutations in the perforin gene related to T-cell cytotoxicity; both conditions are associated with hypersecretion of pro-inflammatory and Th1 cytokines, including IFN-gamma, IL-1, IL-6, IL-18, and TNF-alpha. In humans, mutations in seven genes encoding proteins involved in cytolytic effector functions have so far been identified that predispose to HLH. However, although most affected patients develop HLH eventually, disease onset and severity are highly variable. Due to the genetic heterogeneity and variable time and nature of disease triggers, the immunological basis of these variations in HLH progression is incompletely understood. Acquired or 'reactive' HLH is related to hematologic malignancy in 72%, infectious disease in 15%, autoimmune disease in 12%, and is multi-factorial in approximately 11% of patients.

Organ dysfunction besides hematologic dysfunction is eventually present in all patients. In many, multi-organ system dysfunction (MOD) eventuates. Hepatic and/or respiratory failure requiring mechanical ventilation are very common (>80%), and in many cases cardiovascular failure and shock supervene (70%). Many manifest neurologic dysfunction including convulsion and coma, and renal failure is present as well, commonly following hemodynamic decompensation or shock. The condition has mortality rates between 18% and 60%. Most deaths occur between 6 and 26 weeks following the onset of the HLH syndrome. Thus, there is typically considerable time during which to establish the diagnosis and undertake immunomodulatory and other treatments.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Embodiments described in this disclosure are directed towards systems and methods for monitoring patients and quantitatively predicting whether or not a deterioration in their health status is likely within a future time interval subsequent to computing a prediction. For example, embodiments may determine a numerical probability of acute deterioration in hospitalized patients, and the future time interval may be within the next 12 to 72 hours. In one embodiment, serial medical data of a particular patient is received from a plurality of inputs. Based on a transformation of the received data, a predicted probability of acute deterioration (PPOD) score is determined. The PPOD score is provided to clinicians, to ensure that timely and effective measures may be taken to mitigate the patient's chances of acute deterioration.

Further, in one aspect, incoming medical data is received from a patient (e.g., through a patient monitor and/or interface), medical datum is transformed into a transformed PPOD value(s), and the transformed PPOD value(s) corresponding to each of the medical datum are combined into a single PPOD value or "score. The predicted probability of acute deterioration (PPOD) score may then be provided to a caregiver; for instance, it may be displayed on a computing device as a PPOD plot over a predetermined time frame, such that a user may identify risk trends in a patient by evaluating said PPOD plot. In this way, embodiments of the disclosure are particular beneficial for patients in whom other acute condition or deterioration scoring systems yield false-negative results.

Yet further, in one aspect, the predicted probability of acute deterioration score may be determined to satisfy a probability threshold and based on the determination the system may perform an action that may alter and or enhance the care provided to the patient. For instance, the system may enter new orders, change orders, and/or prevent specific orders from being entered during the future time interval. Further, in one aspect, the action(s) performed by the system may be based on the degree to which the score exceeds the threshold probability. For instance, scores that exceed the threshold probability may be stratified into classes, subclasses, ranges, sets, and/or subsets wherein one or more actions are associated with each group.

BRIEF DESCRIPTION OF THE DRAWINGS

The present invention is described in detail below with reference to the attached drawing figures, wherein.

Figure 1A:
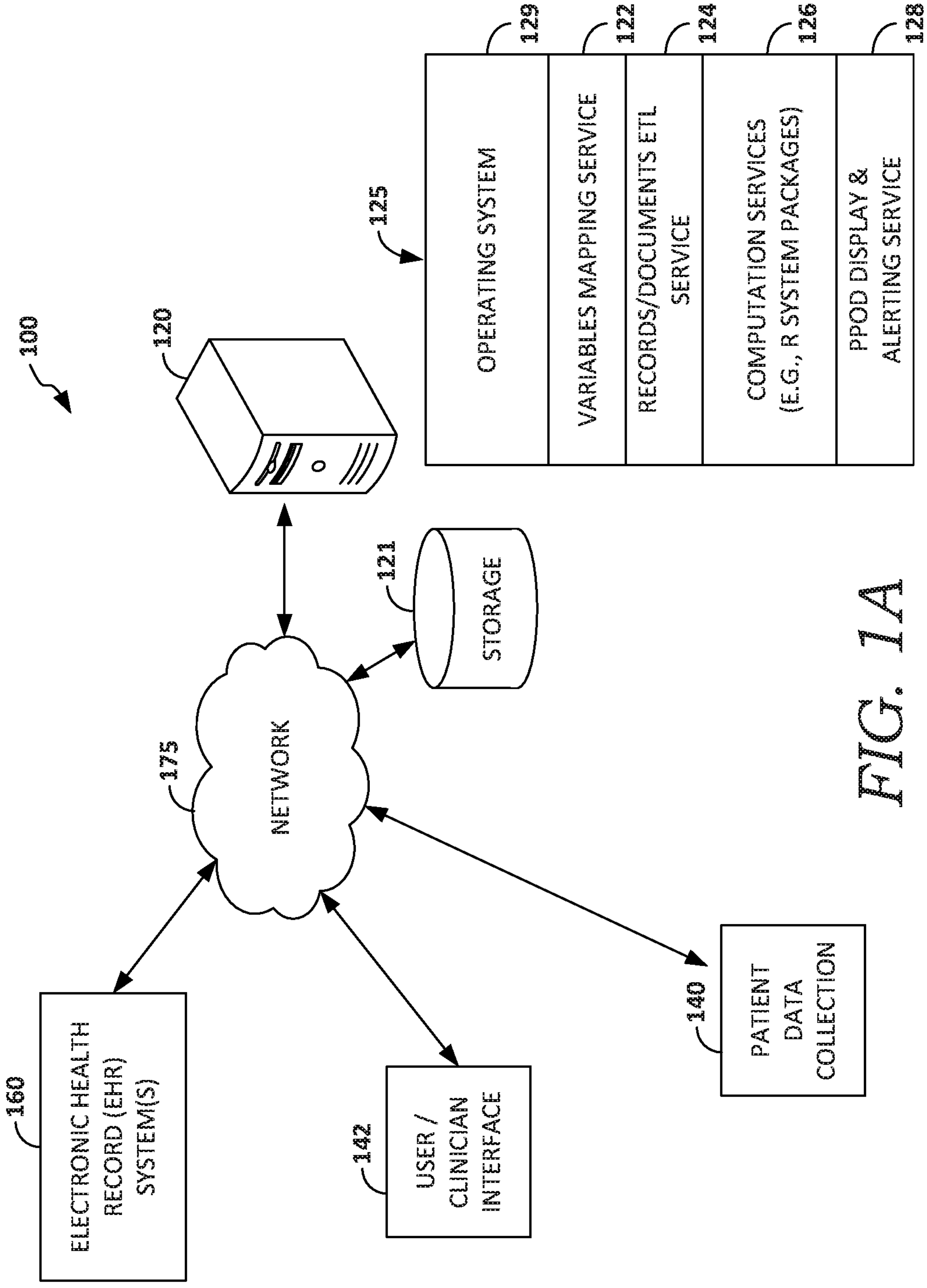
FIGS. 1A and 1B depict aspects of an illustrative architecture suitable for practicing an embodiment of the invention.

FIG. 6A illustratively provide an example embodiment of a computer program routine for performing the HLH copula regression utilized to determining a numerical probability of acute deterioration; and FIG. 6B depicts a look-up table of probabilities utilized by an example predictive model, in accordance with an embodiment of this disclosure.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

As described above, system, methods, and computer-readable media are provided herein for determining a numerical probability of acute deterioration in hospitalized patients. Some embodiments employ a copula analysis that measures the statistical dependency (or lack thereof) between two time series, for instance, a time series of numbers of transgressions of reference threshold values for laboratory and physiologic measurements and a time series of the shock index (SI) denoted by the ratio of synchronously determined heart rate (HR) and systolic blood pressure (SBP). In this way, some embodiments of the disclosure are particular beneficial for patients in whom other acute condition or deterioration scoring systems yield false-negative results.

Specifically, despite the superior sensitivity to accurately recognize patients at-risk whose abnormalities are not obvious, embodiment described herein may simultaneously achieve specificity that is superior to conventional approaches. For instance, in an embodiment, the ROC AUC is greater than 80% in an N=124 sample patient population. In part, this greater accuracy and discriminatory power to classify individual cases correctly is due to the utilization of multivariate copula time series methods, according to an embodiment, which enable inferences based on statistical interrelationships between two or more clinical or laboratory variables measured simultaneously at a plurality of time points.

As further described above, Hemophagocytic lymphohistiocytosis (HLH) is a life-threatening syndrome of immune dysregulation and is classified as primary or secondary according to the underlying etiology. The treatment strategies recommended for acquired vs. familial groups differ substantially. Usually treatment is initiated with dexamethasone 10 mg IV bid, cyclosporine 100 mg IV twice daily, anakinra 100 mg sc once daily, 1 dose of etoposide 100 mg IV, and optionally 3 rituximab infusions (range 1-10) at a median dose of 375 mg/m2, intravenous immunoglobulin (IVIG), and transfusions of blood products as needed to address the patient's cytopenias. To date, it is thought to be impossible to predict the HLH using conventional laboratory tests. HLH is characterized by excessive macrophage and T-cell activation as well as impairment of the ability of natural killer (NK) and cytotoxic T cells to kill target cells. Uncontrolled activation of T cells produces excess IL-2, tumor necrosis factor-alpha, and interferon-gamma. Recent studies show that serum levels of soluble interleukin-2 receptor (sIL2R) and ferritin are useful for differentiating some forms of HLH. However, these laboratory tests are not broadly available and are relatively expensive to perform even in those locations where they are available.

The main clinical features of HLH include high fever, hepatosplenomegaly, cytopenia of two or three of the cell lines in the bone marrow, and the presence of activated macrophages in hematopoietic sites; these constitute the classical HLH criteria. Among the two hemophagocytic syndrome subsets, primary/genetic or secondary/reactive, the latter is the most frequently seen in adults. This condition may be triggered by various underlying conditions such as infection (especially by Epstein-Barr virus (EBV), cytomegalovirus (CMV), or human immunodeficiency virus (HIV)), lymphoid malignancy (B- or T-cell lymphoma), connective tissue diseases, or some drugs. HLH criteria were established by the Histiocyte Society in 2004.

More recently, a multi-variable diagnostic tool, referred to as an HScore, has been proposed. Nine variables (3 clinical

[i.e., known underlying immunosuppression, high temperature, organomegaly], 5 biologic [i.e., triglyceride, ferritin, serum glutamic oxaloacetic transaminase, and fibrinogen levels, cytopenia], and cytologic attributes [e.g., hemophagocytosis features on bone marrow aspirate]) are variables in the HScore. However, HScore and other conventional diagnostic methods are "lagging" indicators and do not positively identify HLH until it is well-established and relatively severe. Combinations of common laboratory parameters, such as the percentage of lymphocytes in the leukocyte differential cell count, elevated lactate dehydrogenase (LDH), elevated serum ferritin levels higher than 50,000 μg/L, and the sIL2R/ferritin ratio are useful for identifying patients with familial haemophagocytic lymphohistiocytosis and for differentiating the underlying etiology of pediatric HLH.

We have determined progressive pancytopenia is the feature most likely to suggest secondary HLH in the patients who develop shock and/or organ system failure. Use of other HLH-2004 diagnostic criteria is hindered by the poor operating characteristics of these tests in critically ill patients. Their usefulness is confounded by the facts that (a) treating physicians' therapeutic maneuvers substantially normalize many of the variables that are part of the HLH-2004 criteria, (b) necessary treatments for an underlying condition such as cancer produces abnormalities meeting the HLH-2004 criteria in a percentage of persons who do not later develop HLH, and (c) intercurrent infection or other comorbid conditions may partially mimic the features of macrophage activation syndromes, including HLH. Physical examination for splenomegaly and/or hepatomegaly similarly has poor statistical performance in terms of predictive accuracy. Bone marrow aspiration is presently the most useful diagnostic test, but frequently yields false-negative results. Additionally, due to its pain and invasiveness, bone marrow aspiration is not generally useful for longitudinal determination of progression or severity of macrophage activation and hemophagocytic syndromes.

Major problems in delivery of safe and effective care services in hospitals involve deficiencies in the quality and continuity of patient care, including the monitoring of each patient's condition over time. Despite recent advances in electronic health records (EHR) systems, the present state of the art in medical care within hospitals still does not in general utilize the accruing medical record information for active, prognostic use-cases, to predict the future status or events or outcomes that are likely to materialize for the patient. Instead, in many scenarios the EHR acts mainly as a passive repository for documenting and storing the information that is generated by each provider and each department, which characterizes the current or previous status or outcomes that have already materialized.

During a typical hospital stay, each patient may see many doctors and many nurses. Such fragmentation of responsibility for the care process challenges the ability of each provider to quickly and accurately grasp the meaning of the constellation of accumulating clinical and laboratory facts about the patient, to understand trends that may be developing in the patient's health status, and to evaluate the urgency of attention that is necessary to effectively address existing or newly developing issues or to successfully prevent potential adverse events and complications.

The consequence of the proliferation of medical information in each patient acute care episode, combined with the all-too-common fragmentation of the care process with responsibilities divided among dozens of provider personnel most of whom do not have deep or longstanding familiarity with the patient, is that unexpected physiologic deterioration occurs to many patients, especially post-operatively or post-medical procedures, such that a medical crisis ensues. Precious care resources of the hospital are diverted in an attempt to save the patient, and needless suffering and even death occur. In many such instances, the impending deterioration could have been predicted-provided that enough vital signs and other monitoring data were acquired in advance; provided that that data were integrated into a suitably accurate personalized predictive model; and provided that the output of the model were effectively communicated to the providers who have the responsibility to intervene and prevent or manage the predicted risk of acute deterioration.

While the recognition and interpretation of some acute events such as loss of consciousness or dyspnea or new onset of fever or decompensation of blood pressure or other hemodynamic parameters are clear-cut, in other cases the events or changes are not readily recognized or interpreted, particularly by personnel who have not previously been involved in the patient's care. A change in systolic blood pressure (SBP) to 180 mm Hg might for one person be of ominous and critical significance (for example, in a person whose usual SBP is 110 mm Hg), but carries no adverse prognostic significance for a person whose chronic, poorly controlled hypertension is associated with a usual SBP of 190 mm Hg.

Life-threatening deterioration of patients' health status while in a hospital is often preceded by abnormalities in hemodynamic variables and organ-system parameters measured by clinical and laboratory tests. Over the past several years there have emerged a variety of rapid response team (RRT) and early-warning system (EWS, MEWS, PARS, etc.) methods that aim to combine such information and calculate an index or score that can be used to gauge the risk of acute deterioration and, if the risk is sufficiently high, notify the responsible physicians, transfer the patient to an alternate location where intensified monitoring and care services can be provided, and/or undertake other actions to prevent or mitigate the predicted deterioration.

Frequently, however, there is no obvious or apparent abnormality in vital signs or other clinical or laboratory variables that precedes the deterioration and, in such instances, the RRT- and MEWS-type calculations fail, giving a 'false-negative' assurance that there will be no near-term deterioration in the patient's status when in fact deterioration does materialize. A Hodgetts Score=7 has only a sensitivity of 64%, and Score=8 yields sensitivity of only 52%, for example. In other words, in 36% and 48% of cases, respectively, a false-negative interpretation is ascribed and the Hodgetts score fails to alert the caregivers to the deterioration that ensues.

In other instances, fluctuations in the values of physiologic variables that are utilized by an RRT or MEWS-type calculations give rise to 'false-positive' alarms, incorrectly identifying a given patient as one in whom acute deterioration is likely when in fact no deterioration occurs. In such a situation, valuable resources associated with intensified monitoring or other interventions are misapplied. The resources are allocated to the given patient, in whom those resources are not in fact necessary and provide no benefit, and, insofar as resources are finite and in short supply, those resources are during that same time interval withheld from other patients, for whom the resources might have provided greater value and benefit.

Thus, a significant limitation of a number of existing models and the computer based systems relied upon in conventional approaches for determining or predicting patient deterioration in health is of limited statistical sensitivity and specificity, with substantial false-negative and false-positive rates. Most of the commonly applied regression equations or CART or decision-tree or neural-network or other classification algorithms are able only to achieve receiver operating characteristic (ROC) area-under-the-curve (AUC) discrimination performance of approximately 75% to 80%. Certain existing models achieve ROC AUC of up to 90% in selected subpopulations, such as patients in an emergency department.

Another significant limitation of conventional approaches is that the variables that are included in the predictions are often temporally 'lagging indicators' (such as serum creatinine or other metabolic indicators of kidney function), which broadly characterize a background of diminished organ-system capacity or organ-system vulnerability to physiologic stressors. But it is a background that is at the time of calculation of the RRT- or MEWS-type score already obvious to the physicians who are managing the patient's care. The RRT- or MEWS-type score does not tell the physicians anything that they do not already know. The same is also true for variables that are not temporally 'lagging' ones. In other words, existing computer-based systems are incapable of performing the needed and desired functions described herein.

For example, 'threatened airway' (or 'respiratory rate<5 bpm or >30 bpm') is included in several conventional models, but this is not a variable that should require elaborate calculations to interpret, nor should decision-making regarding whether to intervene or intensify monitoring of the patient await computation of a multivariable score that incorporates such variables.

An acute change in mental status (such as is often measured by Glasgow Coma Score or other scales) is likewise intuitively obvious with regard to portending increased risk of further deterioration or adverse events. An acute change in body temperature is another example of a self-evident or 'obvious' indication of acutely altered risk of acute deterioration. The risk that is entailed by such information is obvious on its face, and an index or score that references these variables adds little value toward prediction or anticipatory decision-making to prevent declining health or to manage adverse events that have not thus far materialized. Such 'obvious' information and scores derived from them primarily serve (a) as a post-facto form of concise documentation of the materialized abnormalities and associated, already-obvious increased risk and (b) as a means of triaging or prioritizing patients according to already-materialized severity of illness.

Still further, another limitation of the conventional technologies is that the predictive models typically rely upon measurements that are often performed in an imprecise and inconsistent manner. For example, measurement of diastolic blood pressure (DBP) by auscultation of Korotkoff sounds with a stethoscope and blood pressure cuff ought in principle to be a relatively accurate and precise process. However, haste and poor technique on the part of the observer often cause DBP measurements to be in error by many millimeters of mercury. It is difficult to compel improvements by busy caregivers who are prone to make imprecise and inconsistent measurements. As a result, any point-estimate or single-point-in-time predictor that is based on variables whose values tend to be subject to inaccuracy, imprecision and inconsistency in measurement technique tend to generate wide variations in predicted risk. By contrast, variables whose measurements do not present such difficulties (such as systolic blood pressure SBP and heart rate HR) are amenable to more accurate, precise predictions.

Yet a further limitation of the conventional technology is that the predictive models fail to take into account inflammatory conditions that may be the cause of subsequent multi-organ system failure and hemodynamic instability, such as cytokine storm and macrophage activation disorders.

Therefore, for the foregoing reasons, the improved systems and methods provided by embodiments of this disclosure for ascertaining the presence of a macrophage activation syndrome and determining or predicting its severity in terms of acute probability of deterioration or organ system failure are valuable and needed. Further, the application of the embodiments described herein lead to a significant improvement in patient outcomes, clinical support systems, and the health-care industry in general. Thus, by employing the techniques, systems, and methodology described herein, some embodiments overcome the deficiencies in the conventional practice by providing entirely new functionality to the clinical support systems and the digital healthcare network environment by creating new predictive and analytical tools previously unknown in the field. Some embodiments overcome the deficiencies that are associated with the conventional industry practice by gathering particularized data from unique data sources and relying on unconventional techniques to overcome the tragically fatal deficiencies found within prior industry practice.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the disclosure, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors or sensors, for example.

Example operating environment 100 further includes one or more user/clinician interfaces 142 communicatively coupled through network 175 to an EHR system 160. In various embodiments of environment 100, one or more user/clinician interfaces 142 may be located in an in-hospital environment, remotely located from the patient, or both. Further, although environment 100 depicts an indirect communicative coupling between interface 142 and EHR system 160 through network 175, it is contemplated that an embodiment of interface 142 is communicatively coupled to EHR system 160 directly.

An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A caregiver/clinician application facilitates accessing and receiving information from a user or health care provider about a specific patient, set of patients, or provider clinicians, according to the embodiments presented herein. Embodiments of interface 142 also facilitates accessing and receiving information from a user or health care provider about a specific patient or population of patients including patient history; health care resource data; variables measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

As shown in example environment 100, user/clinician interface 142 is communicatively coupled through network 175 to EHR 160 and patient data collection 140. In an embodiment, patient data collection 140 communicates via network 175 to computer 120 and/or provider clinician interface 142. In an embodiment of patient data collection 140 (sometimes referred to herein as patient monitor, bedside monitor, or measuring device) comprises one or more sensor components operable to receive or acquire clinical or physiological information about a patient, such as various types of physiological measurements, physiological parameters or variables, or similar clinical information associated with a particular physical or mental state of the patient, and which may be acquired periodically or as one or more time series. In an embodiment, one or more sensor components of patient data collection 140 may comprise a user-wearable sensor component or sensor component integrated into the patient's environment. Examples of sensor components of such embodiment of patient data collection 140 include a sensor positioned on an appendage (on or near the user's head, attached to the user's clothing, worn around the user's head, neck, leg, arm, wrist, ankle, finger, etc.); skin-patch sensor; ingestible or sub-dermal sensor; sensor component(s) integrated into the user's living environment (including the bed, pillow, or bathroom); and sensors operable with or through a smartphone carried by the user, for example. It is also contemplated that the clinical or physiological information about patient, such as the monitored parameters or variables and/or clinical narratives regarding the patient, used according to the embodiment of the invention disclosed herein may be received from human measurements, human observations, or automatically determined by sensors in proximity to the patient. For example, in one embodiment, a nurse periodically measures a patient's physiological variables, such as blood pressure or other variables described herein, and enters the measurement and/or observations via patient data collection 140 or interface 142. In another example, a nurse or caregiver enters one or more progress notes for an in-patient via patient data collection 140 or interface 142.

Examples of physiological parameters or variables received via patient data collection 140 can include, by way of example and not limitation, heart rate, blood pressure, oxygen saturation (SoO2), central venous pressure, other vital signs, other laboratory or physiological parameters described herein, or any type of measureable, determinable, or observable physiological or clinical variable or characteristic associated with a patient, which in some embodiments may be used for forecasting a future value (of the measured variable, a composite variable based on one or more measured variables, or other factor determined at least in part from one or more measured variables) of a patient in order to facilitate clinical decision making. For example, in some embodiments, patient data collection 140 may be used for acquiring, determining, or characterizing (by a human caregiver) other types physiological variables such as, muscle activity which might be sensed from electromyogram signals, eye movement which might be sensed from electro-oculogram signals, or other biometric information. In an embodiment, patient monitor 140 collects raw sensor information and performs signal processing, such as velocity measurement, forming a physiological variable decision statistic, cumulative summing, trending, wavelet processing, thresholding, computational processing of decision statistics, logical processing of decision statistics, pre-processing or signal condition, etc., part or all of which may be performed on patient data collection 140, interface 142, and/or computer system 120.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages, such as gcmr package for determining Gaussian copula marginal regression models, or similar program routines or libraries, natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIG. 6A. In some embodiments, computation services 126 use EHR 160 and/or PPOD display and alerting service 128. PPOD Display and alerting service comprises services or routines for presenting PPOD scores and related information to caregivers or for emitting alerts, which may be communicated, displayed, or otherwise provided to caregivers when likelihood of patient deterioration is determined.

Some embodiments of stack 125 may further comprise model data and model storage services (not shown) and may use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
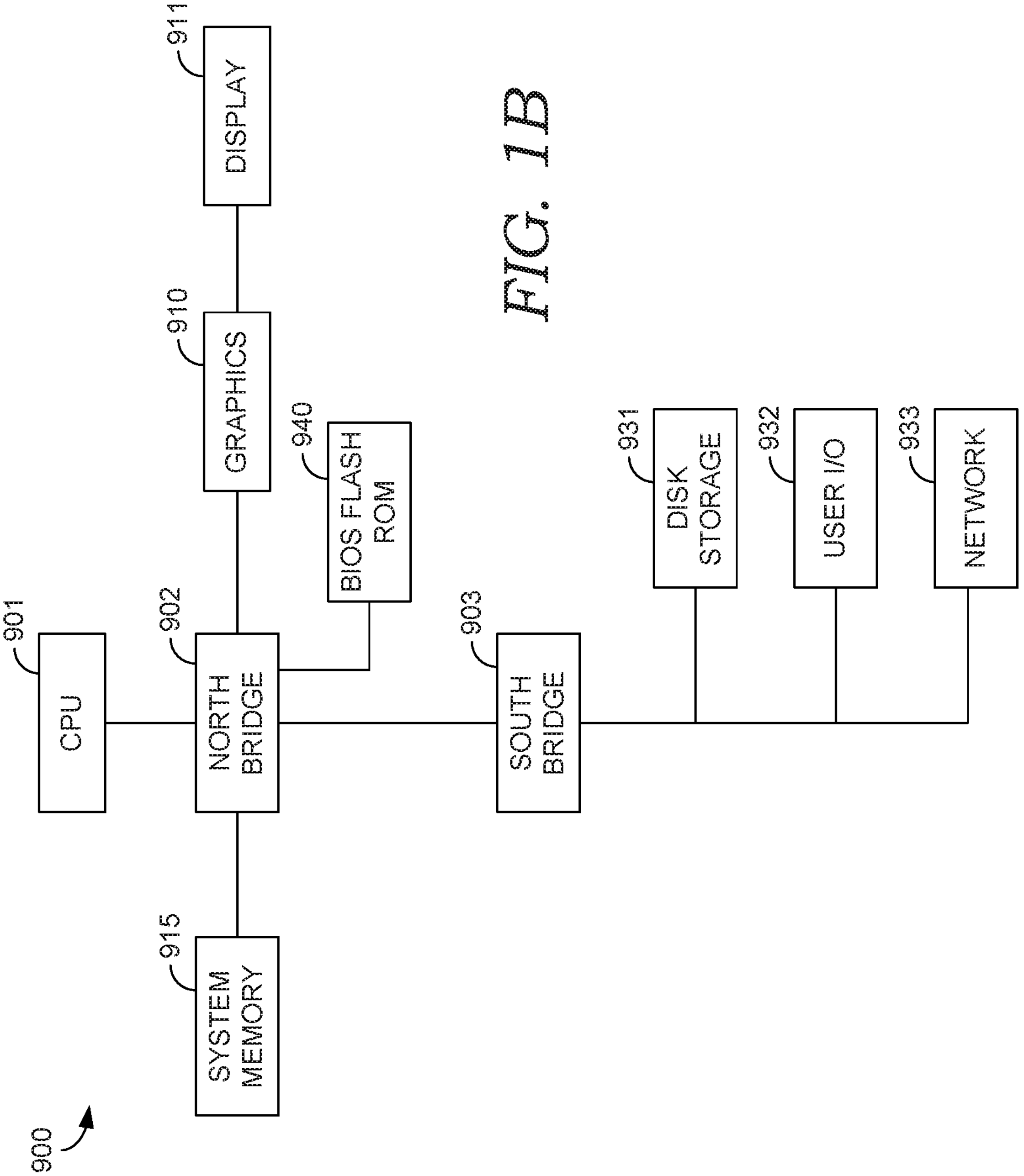

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

With reference now to FIG. 2 and more generally to FIGS. 3A-6B, a flow diagram is provided in FIG. 2 illustrating a method 200 for determining a numerical probability of acute deterioration, using a PPOD score, in hospitalized patients as a result of a macrophage activation disorders. Various patient deterioration early-warning systems (e.g., EWS, MEWS, PARS) may be used to determine a patient's need to be transferred to the ICU by providing an emergency 'alert' notification via email or SMS text message or by other means, to the attending physician and to Rapid Response Team staff, who then undertake appropriate review and decisions as indicated. However, many conventional RRT- and EWS-type systems are point-estimate predictions at a point in time and do not convey longitudinal trend information. Moreover, they are limited in the number of factors analyzed and thus are quite insensitive to a broad range of health conditions that account for a substantial proportion of the deterioration events that arise.

For example, a patient whose heart rhythm is prone to become rapid (nonsustained ventricular tachycardia; NSVT) may be at risk for life-threatening cardiac arrhythmias. In many such patients, the body's circulatory system has sufficient hemodynamic reserve and resiliency to tolerate NSVT for extended periods of time. But in other patients, the hemodynamic reserve may be deficient, or the baroreceptor response sensitivity may be impaired, or other abnormalities may exist such that NSVT is poorly tolerated even briefly, producing a cascade of interrelated cardiac ejection and conduction derangements, leading to life-threatening cardiac events. None of the prior art RRT- or EWS-type systems collect or analyze variables so as to be able to ascertain the ability to tolerate NSVT or other transient stresses. Thus, the application of embodiments described herein provides a significant improvement to prior technical systems developed to address this problem.

There are some deterioration events that are acute, with sudden onset and no apparent antecedent abnormality or multivariate cluster of abnormalities that predict the imminent event. Fortunately from the screening and diagnostic perspective, a majority of patients who deteriorate have a prodrome of hemodynamic and other abnormalities for many hours in advance of the onset of acute deterioration. This affords a 'window of opportunity' sufficient for undertaking effective preventive and corrective actions and intensified monitoring so as to intervene more quickly and effectively than would otherwise tend to occur.

The practical reality, however, is that statistical tests of the goodness-of-fit of distributions to data require a considerable number of observations in order to produce a reliable conclusion or p-value. In one exemplary embodiment of the disclosure actually reduced to practice, the model development dataset and model validation dataset were able to generate stable, reliable p-values for copulas consisting of 6 or more sets of measurements. Accordingly, the embodiments discussed herein achieve superior predictive accuracy and statistical discrimination by processing the resulting array of information so as to generate a predicted probability of acute deterioration (PPOD) from the acquired laboratory and physiologic measurements.

In particular, in some embodiments, the natural logarithm of the mean baroreceptor reflex sensitivity (BRS) obtained over a series of not less than 6 such measurements, the index of the deviation of the patient's current systolic blood pressure from the pressure that is usual for the patient, and the probability $p>0.10$ that the bivariate copula of the autonomically challenged vs. unchallenged heart rate difference time series and the autonomically challenged vs. unchallenged systolic blood pressure difference time series is not different from an extreme-value copula are combined to create a statistical classifier. In one embodiment, these three variables are combined via a logistic regression equation to produce a predicted probability of acute deterioration (PPOD). Other embodiments may utilize alternative variable-combining algorithms and equations (such as neural-network, CART classification and regression tree, decision-rules, support-vector machine algorithms, etc.) to achieve a comparable classification or predicted probability. For example some embodiments may combine the natural logarithm of the mean baroreceptor reflex sensitivity, interbeat interval (IBI) difference calculated from supine and 60-degree tilt heart rate measurements, the quadratic function of the absolute value of the difference between the current SBP and the patient's usual SBP, and one or more time series of physiologic and/or biologic measurements via a logistic regression equation to produce a PPOD.

Computation of Risk of Acute Deterioration

Copulas are a way of quantitatively characterizing the mutual and joint statistical dependence structures of vectors of multiple random variables. Although copulas have been studied for decades, they were not extensively applied until relatively recently. Interest in copulas has been renewed recently in biostatistics, reliability engineering, and financial engineering, and other fields.

Modeling multivariate longitudinal data is an important challenge in biostatistics. According to convention, models tend to assume that the original data or some transformation of them are multivariate normal with a variance-covariance matrix structured to describe serial dependence, heterogeneity and dependence between response variables. Unfortunately, normality is certainly not a rule in practice, particularly with physiologic variables. When the responses are not normally distributed, and when their marginal distributions are not in the same family, alternatives to the multivariate normal must be found.

Very few tools exist to model such data. One approach considers, at each time point t, a model for the mean of each outcome conditional on its history and on the values of the other outcomes at time t. The conditional variance of each outcome is assumed proportional to a fixed function of the conditional mean.

Some tools deal with data of mixed types when the vectors of observations are only observed once on independent or clustered units, for instance, a joint model for mixed continuous and categorical data. It may be extended to deal with missing values in reference. Conditionally on the categorical responses combination (with a marginal multinomial distribution), such approaches assume that the continuous variables are multivariate normal. The EM algorithm may be used to obtain the maximum likelihood estimators (MLEs) in the presence of missing values. One such approach considers a multivariate t distribution instead of the more constraining multivariate normal and by allowing different covariance matrices across cells.

Some models for mixed type data are devoted to the analysis of toxicity studies. These typically involve clustered responses of mixed types. One example is in toxicology. In one approach, such data may be modeled using marginal regression models for each of the responses while treating the intracluster correlation as a nuisance factor. GEEs may be derived to obtain consistent parameter estimates while accounting for intracluster correlation. The parameters from the marginal regression models are robust to dependence misspecification.

In some embodiments of this disclosure, a binary "deteriorated" vs. "did not deteriorate" response is modeled as an unknown copula class of supine and 60-degree tilt IBI difference values and supine and 60-degree tilt SBP difference values. It is determined that patients who do not deteriorate acutely tend to have copulas that are bivariate normally distributed, while patients who do deteriorate empirically tend to have copulas that exhibit dependency that is characteristic of an extreme-value (Gumbel) copula. The physiologic reasons why this is so require further study. However, the statistical association of the "deteriorated" response with the extreme-value copula dependence structure may be empirically utilized in a predictive model regardless whether the mechanism that underlies the association is elucidated. Likely, the mechanism leading to the extreme-value copula dependence between IBI difference and SBP difference under conditions of autonomic challenge has to do with altered sympathetic and/or parasympathetic vascular tone or with acute alteration of baroreflex sensitivity and consequent acutely altered hemodynamic compensatory capacity.

In some embodiments, a single term in the predicted probability of acute deterioration formula may contain multiple medical data inputs. For example, as noted in the above incorporated discussions of PPOD various medical readings (supine and 60-degree tilted SBPs, *IBIs*, etc.) are each transformed before fitting a 12-point copula and calculating the PPOD value. It is understood however, the multiple medical data inputs may be combined before being transformed, such that the transformed numbers used for forming a portion of the PPOD, are a combination of multiple health readings.

In one aspect, a joint model may be built for clustered binary and continuous outcomes with an application to developmental toxicology. An extension of the correlated probit model may be used to obtain a joint distribution for the binary and the continuous responses. A joint multivariate normal distribution may be considered for the corresponding latent variables and each outcome is analyzed with a marginal dose-response model. The covariance matrix takes into account the correlation between outcomes and the correlation due to clustering. This is an improvement where model estimates of the correlation between responses and the evolution of these correlations with dose are available. A marginal approach is preferred to conditional models with the arguments that the biological mechanism relating the chemical exposition to developmental problems is not well understood, and that conditional models are difficult to use to quantify risk or to study the marginal effect of dose on an isolated response.

In some embodiments described herein, copulas are used to model multivariate non-normal longitudinal data. By definition, an n-dimensional copula is a cumulative distribution function with uniform marginals. In the present invention, the three responses were treated as if they were multivariate continuous although the heart rate and blood pressure are integer-valued and essentially discrete. When measured manually, the heart rate is often quantized into discrete values modulo-4, inasmuch as heart beats are typically observed for 15 seconds and multiplied by 4 to obtain the minute-wise heart rate. When blood pressure is measured manually, the pressures are typically recorded in even numbered increments, modulo-2, due to the nature of the sphygmomanometer gauge or quantization of digital display values. These data-conditioning considerations necessitate certain preprocessing to enable the copulas for PPOD calculations to be numerically stable.

Copulas may be used whatever the type and the marginal distribution of the involved variables, but when non-continuous variables are involved, one may use finite differences instead of analytical derivatives of the copula to calculate the likelihood values and one may randomly perturb the data values to break ties. In the preferred embodiment, this is done by randomly adding or subtracting a small value from each supine vs. 60-degree-tilt IBI difference and from each SBP difference. The data of relatively healthy patients who do not deteriorate are usually well-fit by the normal copula or by the Frank copula. Indeed, by specifying two correlation matrices (which should be named more generally dependence matrices), we have defined entirely the dependence arising due to the repeated character of our measurements with the first copula and the dependence between the different types of measurements at each time point with the second copula. However, in some embodiments alternative multivariate copulas or copulas other than the normal one may be used.

Except when considering bivariate Archimedean copulas, descriptive and graphical tools are generally unavailable to understand the dependence structure in the data and to make a preselection of appropriate copulas. Accordingly we select our copula(s) in simple parametric families (indexed by one or two parameters) by taking the one giving the largest log-likelihood.

The estimation of the parameters (from the second copula) describing the dependence between the different variables may be made conditionally on the fitted univariate marginal distributions. This uses the argument that continuous margins in a copula model do not depend on the choice of the dependence structure of the data, suggesting that the modeling and the parameter estimations for the margins and the copula can be made separately.

In some embodiments, the bivariate copula of (a) the interbeat interval (IBI) difference calculated from supine and 60-degree tilt heart rate measurements and (b) the supine vs. 60-degree tilt systolic blood pressure (SBP) difference frequently exhibits properties of extreme-value copula (Gumbel copula) dependency and distribution structure in patients who subsequently deteriorate with in an acute period of less than 24 hours, whereas the IBI-SBP difference copula of patients who do not deteriorate shows little dependency between the variables' distributions. The copulas may in principle be of any dimension, but in one embodiment involves not less than 12 contemporaneous IBI and SBP supine and 60-degree tilt values separated by not less than 30 min. In a particular distributed client-server embodiment, an indexing service indexes and maintains buffered (cached) copies of the most recent 12 such sets of values for each applicable hospital inpatient, as well as a cached copy of the usual SBP for each applicable patient, for use in subsequent PPOD computations.

In a set of studies conducted, the copulas of stable non-deteriorating patients are well-fitted by the normal copula or the Frank copula. To insure numerical stability of rank-based copula analytics, the raw values are first perturbed so as to eliminate any 'tied' values by adding or subtracting a small fractional (<0.1) random value from each vector element before forming the bivariate copula of the vectors. The presence of ties in the data substantially affects the estimation of the p-value. Ignoring the ties, by using midranks to compute pseudo-observations or by other methods, can likewise bias the estimate of the p-value. Therefore to solve this problem, some embodiments construct or determine pseudo-observations by randomly breaking the ties, shifting the tied ordinates and abscissas by small random amounts.

Some embodiments may involve statistical testing to determine whether or not the copula of a particular patient is or is not an extreme-value copula, comparing the empirical copula with a rank-based nonparametric estimator of the patient's copula derived under Pickands-type extreme-value dependence. The value of a binomial variable denoting the extreme-value copula predicate may be generated by a variety of computational methods. In an illustrative embodiment, the PPOD inference engine service calls an evTestA function in the open-source R statistical package with multiplier iterations count of at not less than 1,000. The determination of extreme-value dependence structure, as is done in the illustrative embodiment by the R evTestA function, returns the test statistic and the p-value of the test statistic. If the p-value is greater than 0.1, the extreme-value copula predicate value is set equal to 1. Otherwise, it is set to zero. The value of the extreme-value copula predicate variable is one variable that is employed in calculating the PPOD probability. A second variable, the natural logarithm of the mean baroreflex sensitivity [In (mean (BRS)), in log msec/mmHg], may be computed from the same array of supine and 60-degree tilt IBI and SBP measurements. A third variable, the index of the deviation of the current SBP from the patient's usual SBP may be computed as a quadratic function of the absolute value of the difference between the current SBP and the patient's usual SBP. In some embodiments, the PPOD may further utilize root mean square of successive deviations (RMSSD) of a time series of physiologic and/or biologic measurements as a surrogate nonparametric measure of the high-frequency power spectral density (PSD) to identify strong statistical associations with the presence, near-term future emergence of macrophage activation syndromes, and/or the severity of macrophage activation syndromes. Utilizing these input variables, a model(s) having satisfactory predictive accuracy may be constructed using linear discriminant analysis (LDA), gradient boosting, random forest (RF), neural network, logistic regression, and/or other, similar classification or regression models. In some embodiments, time series of physiologic and/or biologic measurements may comprise at least one time series of heart rate, systolic blood pressure, ferritin, fibrinogen, LHD, triglyceride, erythrocytes, leukocytes, platelets, albumin, lactate dehydrogenase, creatinine, resting respiratory rate, resting heart rate, the natural logarithm of the mean baroreflex sensitivity, the index of the deviation of the current SBP from the patient's usual SBP, the extreme-value copula predicate variable, and/or body temperature measurements.

In one illustrative client-server embodiment, the PPOD probability may be calculated via a logistic regression equation (an illustrative portion of which is shown as Eq. 1, below) in which the values of these variables appear as terms:

$$index = 1.89 * (nbr\_transgr - 1.64) \quad \text{(Eq. 1)}$$

$$PPOD = \frac{e^{(-0.000037+1.700592*index+0.000024*index2)}}{\left(1+e^{(-0.000037+1.700592*index+0.000024*index2)}\right)}$$

and the resulting PPOD value is returned (a) to the inference engine whose rules and processes may undertake real-time notification of responsible physicians and nurses via email, SMS text message, or other appropriate means of notification, and (b) to the calling client application program for display to the clinician user or for trend plotting or other uses. The PPOD threshold at which notification alerts are emitted may be determined at the health care organization's (e.g., hospital's) discretion, depending on the epidemiology of acute deterioration incidence rates, staffing levels of clinician individuals able to respond to such notifications, and other factors, as those skilled in the art will appreciate. In one embodiment, the threshold for notification is PPOD>0.50.

In some instances, Eq. 1 may be recalibrated for patient populations that differ substantially from the populations whose study led to developments of the embodiments disclosed herein. For example, the PPOD may optionally be recalibrated to each hospital in which it is implemented. Most hospitals have slight differences in procedures, standards, requirements and other elements of daily practice as compared to other hospitals and some embodiments of the present invention may be adapted to a specific hospital's preferences. By adjusting the PPOD equation according to an individual hospital's procedures, staffing, and patient population, the PPOD may be more accurate.

The process for performing such recalibration may involve accumulation a prospective observational cohort of a sufficient number of patients, both cases who acutely deteriorated and controls who did not, and laboratory and physiologic data from each. In an illustrative embodiment, multivariate logistic regression is performed on a randomized subset of such data, to calculate localized values of the intercept and the coefficient for each of the three variables. Then the other cases and controls that were not included in the first randomized subset are utilized as a confirmatory 'validation' subset and logistic regression is performed on these. If the intercepts and coefficients are in substantial agreement in the 'model development' and 'model validation' regressions, then the new localized model is accepted and its values replace the default values in the PPOD equation. If the intercepts and coefficients are discordant, then the process of accumulating additional cases and controls continues. The monitoring of a clinically unstable patient may be associated with an appropriate treatment to improve care, which can only occur following an appropriate medical review triggered by a meaningful communication by the bedside nurse to physician.

Figure 2A:
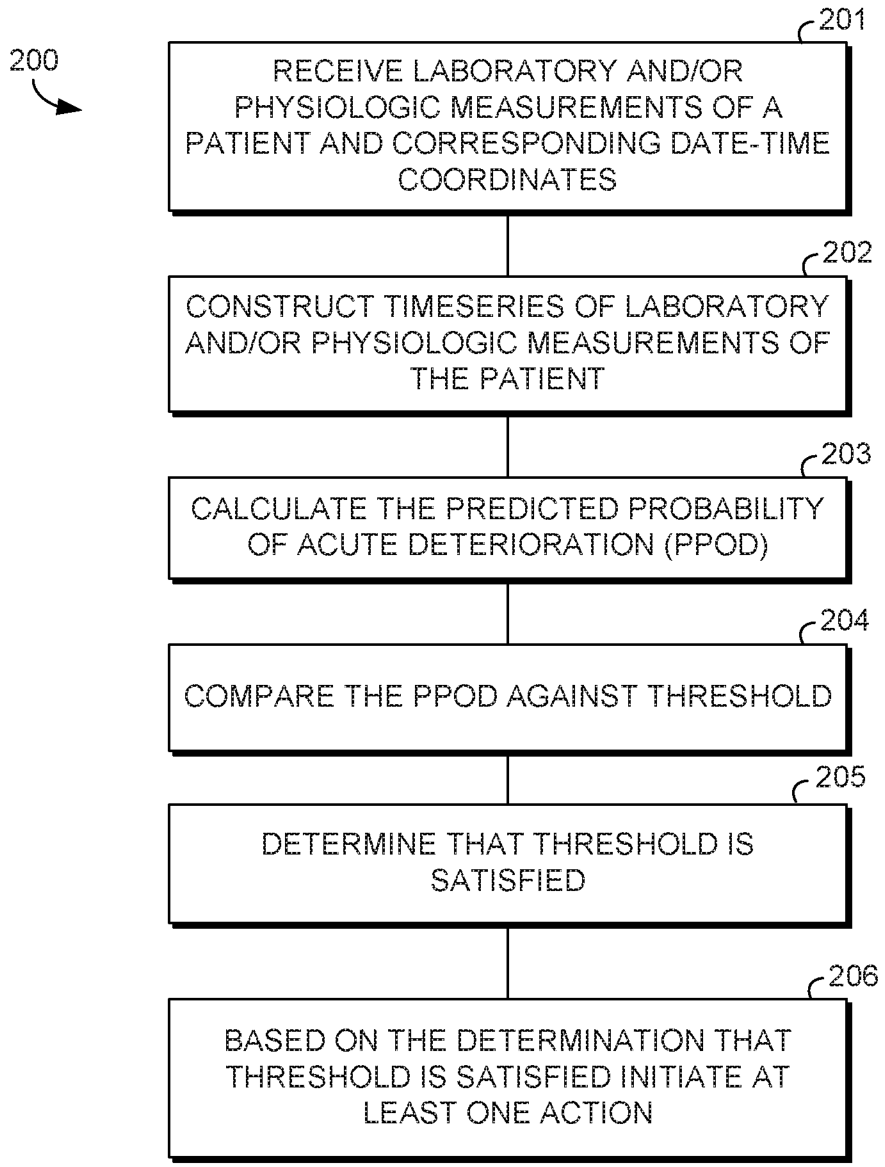
FIGS. 2A and 2B depict a flow diagram of an exemplary method for determining a numerical probability of acute deterioration in hospitalized patients, in accordance with an embodiment of this disclosure.

Turning to FIG. 2A, an exemplary method 200 is provided for determining the numerical probability of acute deterioration in hospitalized patients. At a high level, embodiments of method 200 receives medical data of a particular patient; transforms the data; determines a predicted probability of acute deterioration; and, at least partially based on predicted probability of acute deterioration perform an action. In some embodiments, the action may be notifying the responsible care provider; placing new order(s) in the patient's EMR; altering the patient's care plan; reserving resources, for the patient, in the care facility needed to treat and/or manage the predicted macrophage activation disorder(s); preventing and/or interrupting discharge orders from being submitted for the patient until such time as a responsible care provider has reviewed method 200's results and disabled the automatic discharge prevention measure(s); ordering increased monitoring of the patient; ordering increased testing of the patient; and/or ordering prescriptions for the patient; issuing an electronic alert or notification to the a responsible care provider and/or patient.

In an embodiment of method 200 a series of a single laboratory biomarker and/or physiologic measurement may be used. In an embodiment of method 200, a series of at least two laboratory biomarkers and/or physiologic measurements may be used. In an embodiment of method 200, a series of a plurality of laboratory biomarkers and/or physiologic measurements may be used. Examples of suitable laboratory and physiological variables are described previously, and in some embodiments, patient data collection 140 is utilized to measure the variables of method 200. The variables may be recorded in the patients' electronic health record 160. In some embodiments, as discussed in more detail below, the series need not be "complete" prior to initiation of method 200. Some embodiments of method 200 may be facilitated, at least in part, by a computer program routine illustratively shown in FIG. 6A and/or may use a model probability lookup table such as the example depicted in FIG. 6B.

At step 201, receive laboratory and/or physiologic measurements of the target patient(s) and corresponding date-time coordinates. In an embodiment, step 201 comprises measuring (or receiving) the most recent laboratory in physiologic measurement(s) and corresponding date time coordinate(s). Embodiments of step 201 may be facilitated using patient data collector 104. Additionally, and/or alternatively, embodiments of step 201 may be facilitated by using EHR 160 and/or any electronic health record communicatively coupled with network 175. As such, embodiments of step 201 may access/receive laboratory and/or physiologic measurements of the patient from healthcare facilities, and/or laboratories, other than the healthcare facility where the patient is currently located. For example, the most recent laboratory or physiologic measurement and corresponding date time coordinate may be a laboratory or physiologic measurement taken by the patient's primary care physician at the primary care physician's office and stored in the primary care physician's electronic health record system. At some later point in time, the patient may be admitted to a hospital wherein an embodiment of method 200 may be performed. Upon reaching step 201, the laboratory or physiologic measurement(s) stored in the primary care physicians electronic health record system may be accessed through the network 175.

In an embodiment, step 201 further comprises identification of at least one patient for whom method 200 shall be performed. In an embodiment, the at least one patient may be identified automatically based on predetermined criteria, a rule, a rule set, a machine learned model, a predictive algorithm, and/or the like. For example, at step 201 a system may determine it appropriate to perform embodiments of method 200 on the entire patient population, a subpopulation, or an individual patient of a hospital at set intervals, continuously, or as the requisite patient measurements are acquired.

In an embodiment, the at least one patient may be identified manually through a communicatively coupled user interface (such as user/clinician interface 142). In some embodiments of step 201, the retrieval and/or receipt of the laboratory and/or physiologic measurement values and corresponding date-time coordinates may be facilitated by a communicatively coupled patient data collection system (such as patient data collection 140) and/or a communicatively coupled electronic health record system (such as electronic health record system 160).

At step 202, construct a time series of the laboratory and/or physiologic measurements of the target patient(s). In embodiments, the time series is constructed of the measurements acquired in step 201. The time-series may comprise previous measurement values and their respective measurement date-time coordinates. Some embodiments of step 202 further comprise constructing a time series by appending the most recent measurement values determined in step 201 to the previous time series retrieved in step 202 thereby forming an updated time series.

In an embodiment, the time-series may comprise measurements acquired at, at least, $T_x$ minute intervals. In some embodiments, $T_x$ is equal to 30 minutes. In some embodiments, $T_x$ is equal to 120 minutes. As such, a first measurement may be acquired at $T_0$, a second measurement may be acquired at $T_1$, wherein $T_1 \geq T_0 + T_x$ minutes. A third measurement may be acquired at $T_2$, wherein $T_2 \geq T_1 + T_x$ minutes; and so on. Additionally, in an embodiment, measurements acquired between the $T_x$ minute intervals may be included in the time series. For example, the first measurement may be acquired at $T_0$; $n_0$ measurement(s) may be acquired between $T_0$ and $T_1$; the second measurement may be acquired at $T_1$; $n_1$ measurement(s) may be acquired between $T_1$ and $T_2$; the third measurement may be acquired at $T_2$; and so on. As such, the time series may include at least the first measurement, no measurement(s), the second measurement, $n_1$ measurement(s), and the third measurement, and so on.

Additionally, and/or alternatively, in some embodiments the time intervals ($T_x$) between measurements may be the same duration or may be of varying duration. In an embodiment, the measurements may be acquired within 72 hours. Additionally, in some embodiments, the measurements for a given laboratory or physiologic parameter may be acquired, at least in part, asynchronously from other laboratory or physiologic parameters. For example, measurements for a first parameter may be acquired over a first time period; measurements for a second parameter may be acquired over a second time period; measurements for a third parameter may be acquired over a third time period; measurements for a fourth parameter may be acquired over a fourth time period; and so on. It will be understood by those skilled in the art that the various time periods may overlap, include individual measurements from the same specimen, or may be identical. As such, some embodiments described herein are not reliant on laboratory or physiological measurements made at the same time or with the same patient specimen.

Further, an embodiment of step 202 may comprise determining that the time-series is of sufficient length for the determination of the PPOD. In such an embodiment, when the length of the time series is determined to be of sufficient length the method 200 continues to step 203. Otherwise method 200 waits until the next measurement (step 201) is received and appended to the time series, thereby lengthening it. In an embodiment of step 202, the method 200 continues to wait, receive, and append measurements until such time as a time-series of sufficient length is created.

At step 203 calculate the predicted probability of acute deterioration. In some embodiments of step 203, calculating the predicted probability of acute deterioration may comprise calculating the number of transgressions present within the patient information. Such an embodiment may comprise receiving one or more predictive models; calculating the high-frequency components of the power spectrum or surrogate measurement of the high-frequency power band of the power spectrum from the time series created in step 202; applying the components or surrogate measurements as an input into the one or more predictive models to determine the forecast probability of current and/or future macrophage activation disorders for the patient. In some embodiments, the predictive models may be generated from a population of patients in whom subsequent actual occurrences of a macrophage activation syndrome such as HLH in a defined future time interval were known. Using the models updated with input parameters, a calculated classification and/or forecast probability of current and/or future macrophage activation disorder occurrence within the defined future interval is determined. In some embodiments, step 203 may use the computer program routine illustratively shown in FIG. 6A and/or may use a model probability lookup table such as the example depicted in FIG. 6B.

In some embodiments of step 203, calculating the predicted probability of acute deterioration may comprise calculating the extreme-value copula predicate variable, the natural logarithm of the mean baroreflex sensitivity, and/or the index of the deviation of the patient's the current SBP from the patient's usual SBP. In some embodiments, the number of transgressions, the extreme copula predicted variable, the natural logarithm of the mean baroreflex sensitivity, and/or the index of the derivation of the current SBP from the patient's usual SBP are variables in a logistic regression equation (such as Eq. 1) such that the PPOD value is calculated. Some embodiments of step 203 may be facilitated by computation services 126 and/or variables mapping service 122.

At step 204, compare predicted probability of acute deterioration to a probability threshold. Some embodiments of step 204 compare the PPOD value calculated at step 203 to a threshold. The PPOD value may be compared to one or more threshold probabilities, at step 204. The threshold probabilities may be predetermined by a medical professional or medical care provider or be empirically based. In an embodiment of step 204, the threshold may be a predetermined probability and/or classification. Additionally, in an embodiment of step 204 the threshold may be a predetermined probability and/or classification determined based on the patient's underlying condition(s) and/or the laboratory or physiologic measurements used to construct the time-series and/or calculate the PPOD value. For example, a threshold probability may be established at one value for patients with cancer; a threshold probability maybe established at a second value for patients with an infectious disease; a threshold probability maybe established at a third value for patients with cancer and a comorbid infectious disease; and/or, a threshold probability maybe established at a fourth value for patients with an autoimmune disease. For another example, a threshold probability maybe established for probabilities calculated based on of a first laboratory or physiological parameter (e.g., ferritin); a threshold may be established for probabilities calculated based on of a second laboratory or physiologic parameter (e.g., fibrinogen); a threshold may be established for probabilities based on of a third laboratory or physiologic parameter (e.g., heart rate); a threshold may be established for probabilities based on of a fourth laboratory or physiologic parameter (e.g. the extreme-value copula predicate variable), and so on. For yet another example, a threshold may be established for probabilities calculated based on various combinations of two or more laboratory or physiologic parameters. It will be understood by those skilled in the art that the above referenced examples represent an illustrative subset of possible predetermined thresholds and as such are not intended to limit the scope of this disclosure.

At step 205, determine the predicted probability of acute deterioration satisfies probability threshold. In some embodiments, the probability threshold may be satisfied when, for example, the PPOD value exceeds the threshold probability. In some embodiments, the probability threshold may be satisfied when, for example, the PPOD value equals the threshold probability. In some embodiments, the probability threshold may be satisfied when, for example, the PPOD value is greater than and or equal to the threshold probability.

At step 206, based on the determination that the PPOD value satisfies the probability threshold initiate at least one action. Embodiments of step 206, implement method 200 in a tangible way by using the results of, at least, step 205 to initiate at least one action. In an embodiment, the action may be notifying the responsible care provider; placing new order(s) in the patient's EMR; altering the patient's care plan; reserving resources, for the patient, in the care facility needed to treat and/or manage the predicted macrophage activation disorder(s); preventing and/or interrupting discharge orders from being submitted for the patient until such time as a responsible care provider has reviewed method 200's results and disabled the automatic discharge prevention measure(s); ordering increased monitoring of the patient; ordering increased testing of the patient; modifying the patient's position in a triage list of the responsible care provider(s); ordering prescriptions for the patient; and/or issuing an electronic alert or notification to the responsible care provider(s) and/or patient. Some embodiments of step 206 may be facilitated by EHR systems 160, user/clinician interface 142, and/or PPOD display and alerting service 128.

Figure 2B:
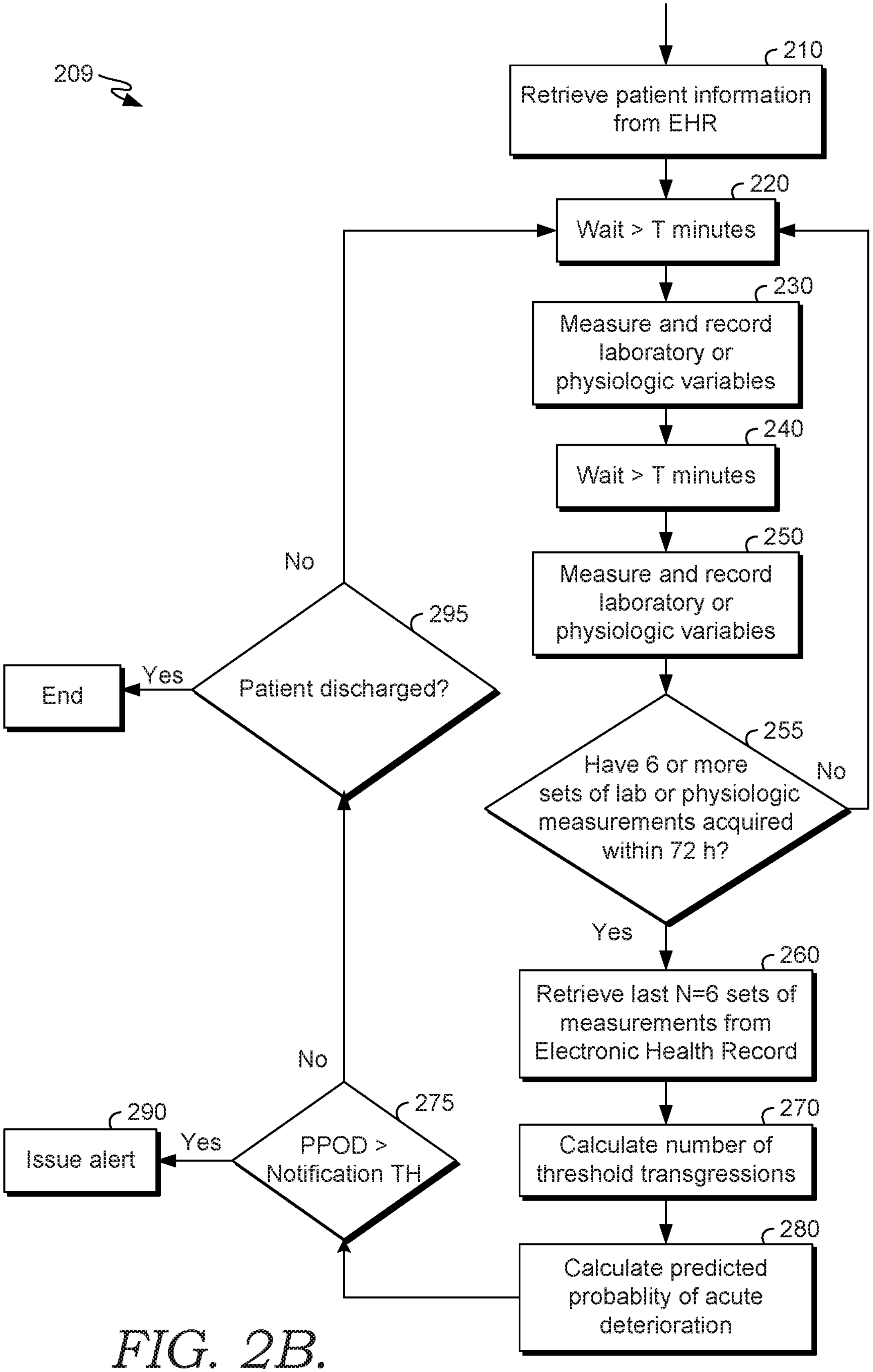

Turning to FIG. 2B and method 209, at a high level, embodiments of method 209 relate to determining a numerical probability of acute deterioration in hospitalized patients. In one embodiment, serial medical data of a particular patient is received from a plurality of inputs. Based on a transformation of the data, a predicted probability of acute deterioration (PPOD) score is calculated. Incoming medical data is received from a patient (e.g., through a patient monitor and/or interface), medical datum is transformed into a transformed PPOD value(s), and the transformed PPOD value(s) corresponding to each of the medical datum are combined into a single PPOD value or "score." The predicted probability of acute deterioration (PPOD) score may then be provided to a caregiver; for instance, it may be displayed on a computing device as a PPOD plot over a predetermined time frame, such that a user may identify risk trends in a patient by evaluating said PPOD plot.

Accordingly, method 209 begins at step 210 where information for a target patient is received from an electronic health record corresponding to the patient. At step 220, method 209 waits for a time frame of T minutes. In one embodiment, T is equal to 120 minutes. In another embodiment, T may be 30 minutes. In some embodiments, the value of T is determined based in part on the specific variables of step 230.

At step 230, measure and record laboratory or physiological variables of the target patient. Examples of suitable laboratory and physiological variables are described previously, and in some embodiments, patient data collection 140 is utilized to measure the variables of step 230. The variables may be recorded in the patient's electronic health record of step 210. At step 240, method 209 waits for a time frame of T minutes, where T may be the same value as in step 220. But it is contemplated that the time frames of steps 220 and 240 are not equal, in some instances.

At step 250, measure and record laboratory or physiological variables of the target patient. Embodiments of step 250 may be performed as described in connection to step 230. At step 255, it is determined whether six or more sets of laboratory or physiologic measurements for the target patient have been acquired within 72 hours. If not, then method 209 returns to step 220 (or step 240) and waits a time frame T to then measure and record an additional set of laboratory or physiological variables. However, if there are at least six sets of laboratory or physiologic measurements acquired within 72 hours, method 209 proceeds to step 260.

Figure 4A:
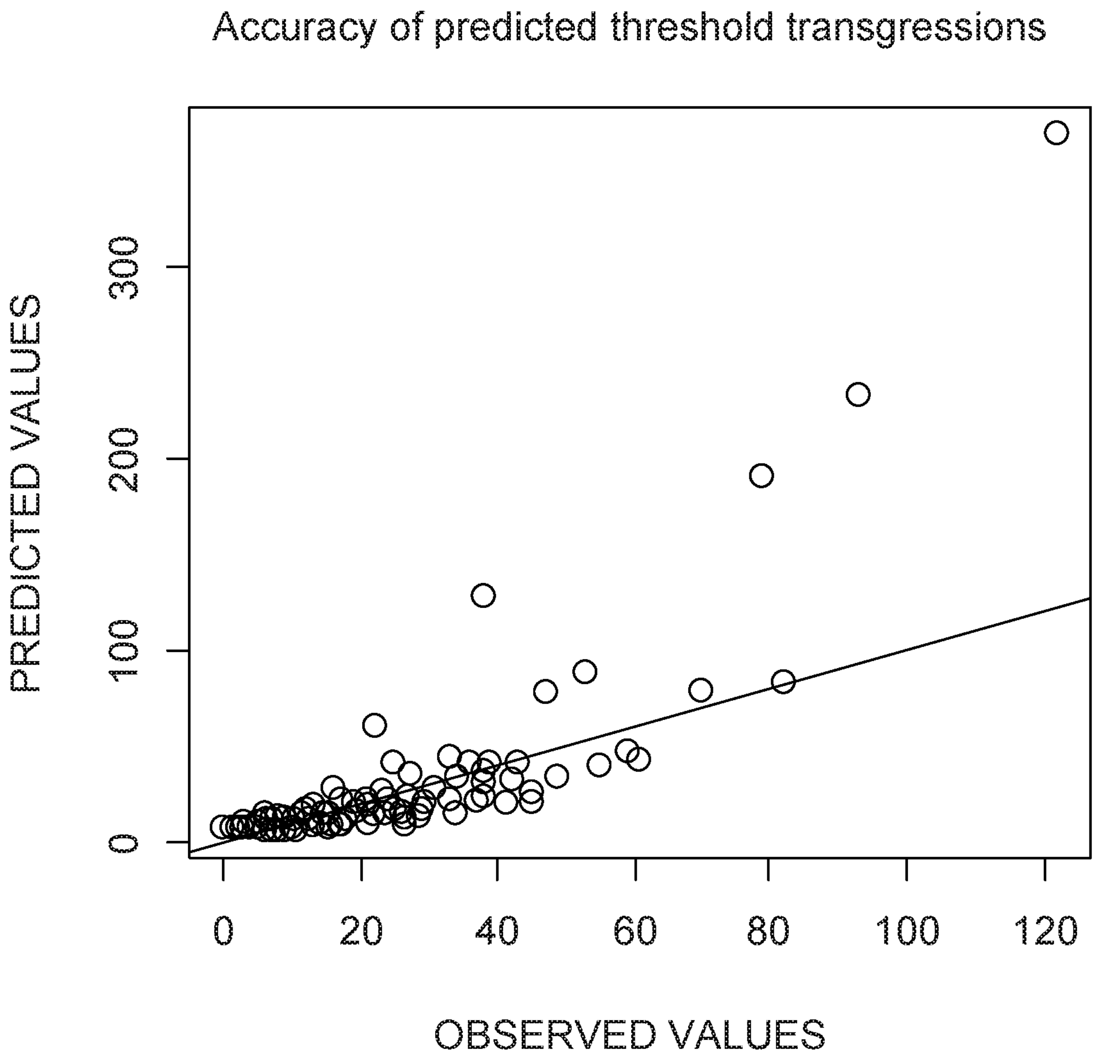
FIG. 4A depicts the copula regression predicted vs. observed number of lab and physiologic values' threshold transgressions for the cohort of N=124 cases for an embodiment reduced to practice.

At step 260, the last six sets of measurements are received from the patient's electronic health record. At step 270, a number of threshold transgressions is determined. FIG. 4A depicts an example of copula regression predicted vs. observed number of lab and physiologic values' threshold transgressions for an example cohort. At step 280, a predicted probability of acute deterioration (PPOD) is determined. A description of determining a PPOD value or score is provided above. At step 275, it is determined whether the PPOD score is greater than a notification threshold. As described above, in one embodiment, the threshold for notification is 0.50 or fifty percent. In another embodiment, the threshold may be sixty percent, for example.

At step 290, if the PPOD score exceeds the notification threshold, then an alert is issued. In some embodiments of step 290, a recommendation is determined or retrieved. Step 290 may provide a specific recommended treatment or thereby, or simply a notification of the prediction or detection, or a combination. In an embodiment, step 290 comprises determining a type of signal or alert to emit, such as an alarm, display, a communication such as an SMS message, or the like. Some embodiments of step 290 provide a personalized advisory message.

At step 275, if the PPOD score does not exceed the threshold, then method 209 proceeds to step 295. At step 295, if the target patient is discarded then method 209 ends. If the target patient is not discharged, then method 209 may return to step 220 and repeat, in an embodiment.

Some embodiments of portions of method 209 may be performed using the computer program routine illustratively shown in FIG. 6A and may use a model probability look-up table such as the example depicted in FIG. 6B. In some embodiments of method 209, a plurality of PPOD scores of various patients relevant to a clinician (provider) or a hospital or practice area may be assembled as a panel of predicted probability of acute deterioration charts, giving a nurse or doctor an overview as to the progress of many patients at one time.

Example Reduction to Practice

With reference to FIGS. 3A-5, and continuing reference to FIG. 2, an example embodiment reduced to practice is now described. Reduction to practice was accomplished using a computer running the Linux operating system (operating system 129), the open-source statistical software package R (software services 126), and the R module (package) gcmr.

Figure 3B:
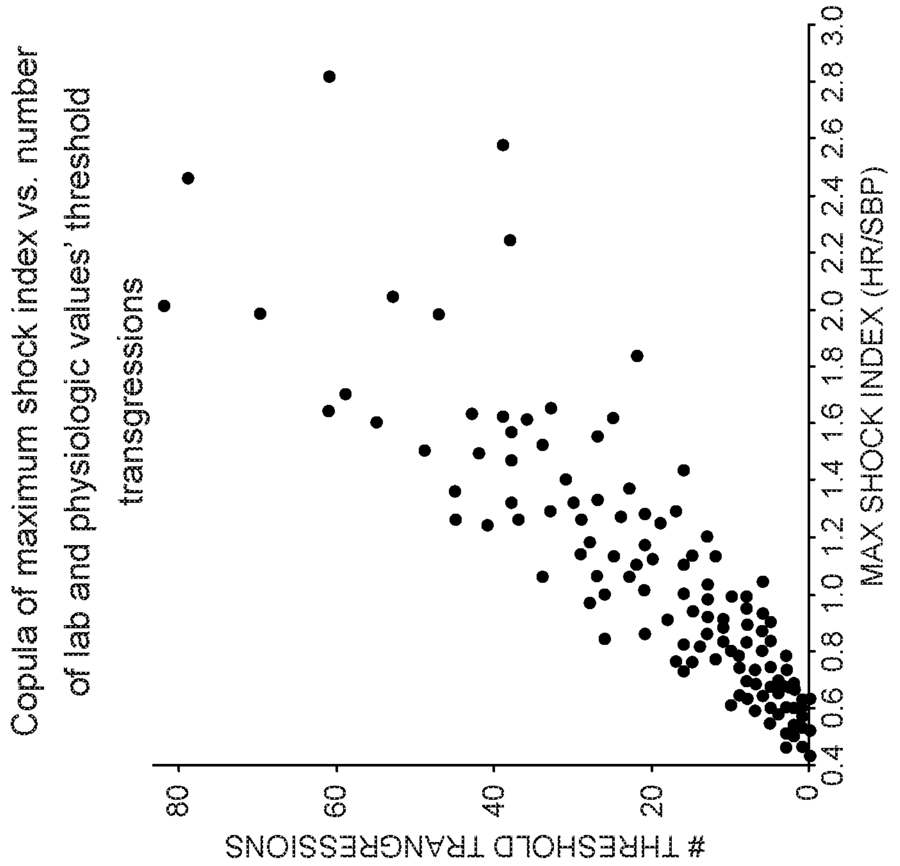
FIG. 3B depicts a bivariate copula relationship of maximum shock index (SI) vs. number of lab and physiologic values' threshold transgressions in the cohort of N=124 HLH in-patient cases utilized in an example embodiment reduced to practice.
Figure 3A:
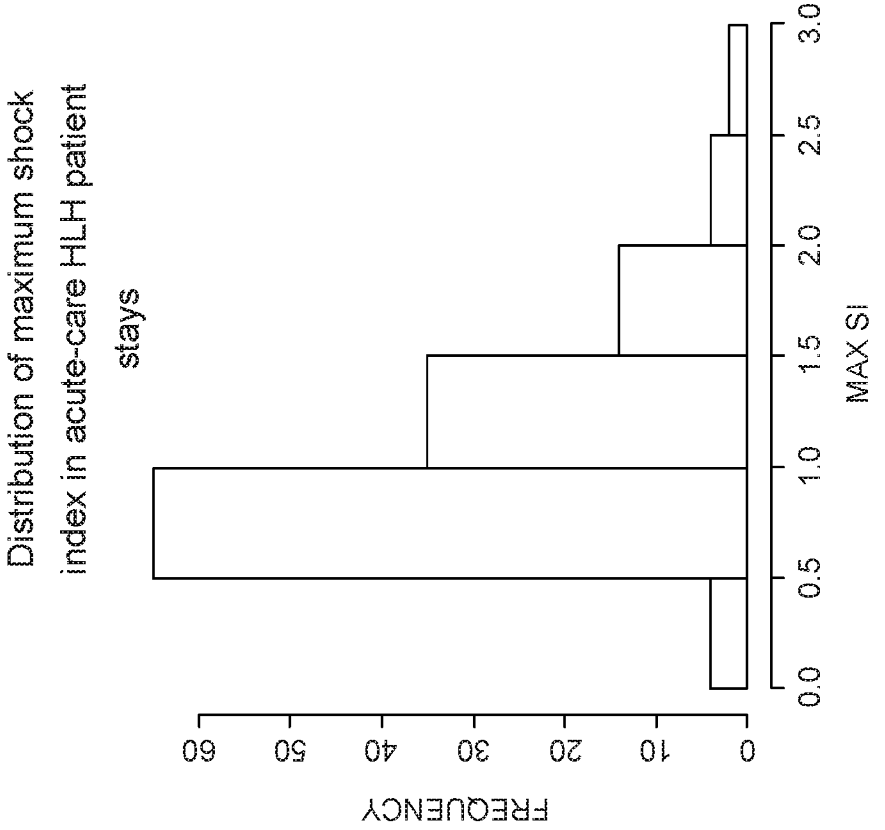
FIG. 3A depicts a representative plot of the statistical distribution of maximum shock index (SI) in N=124 acute-care HLH patient care episodes, in accordance with an embodiment of this disclosure.

For the reduction to practice, an observational study of was performed using a consented, secondary-use-rights-granted data set. Illustrative series of self-monitoring glucometer values were retrieved from a subset of 1,667 HLH patients whose de-identified, confidentiality-protected health records were stored and maintained in Cerner's Health Facts® data warehouse. The cohort selected was comprised of 124 HLH patients for whom Health Facts® contained sufficient serial laboratory and physiologic values measured over a period of not less than 3 days but not more than 180 days. FIG. 3A shows a representative plot of the statistical distribution of maximum shock index for the N=124 cohort of acute-care HLH patient care episodes. FIG. 3B shows the bivariate copula relationship of maximum shock index vs. number of lab and physiologic values' threshold transgressions in the N=124 cohort.

Figure 4B:
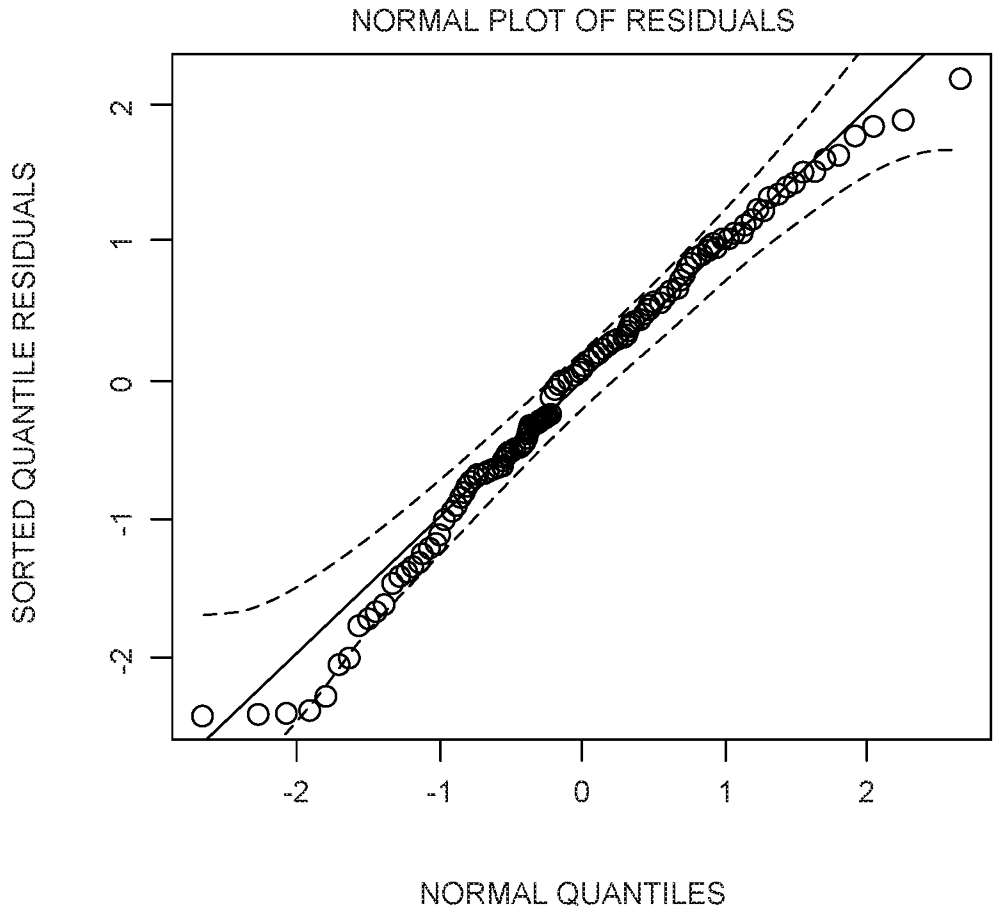
FIG. 4B depicts a copula regression quantile-quantile plot, indicating satisfactory statistical goodness of fitting, for an embodiment reduced to practice.
Figure 5:
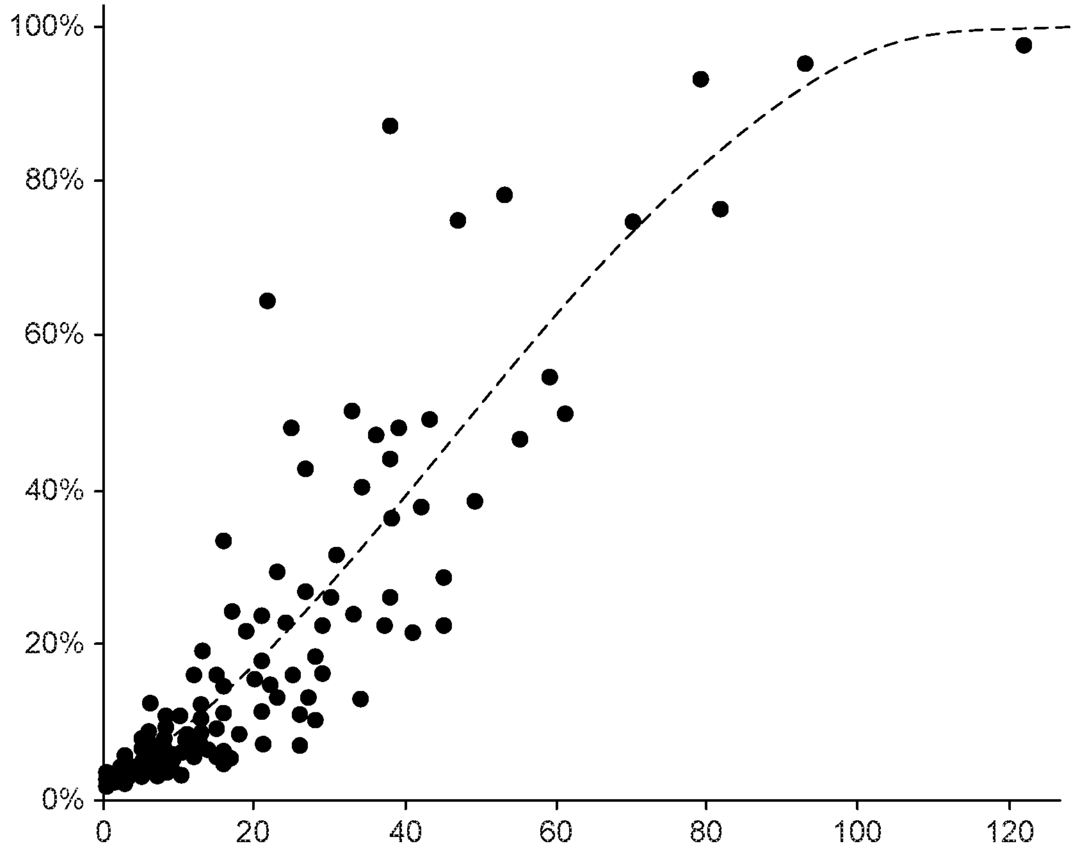
FIG. 5 depicts illustrative example of the copula regression to determine PPOD predicted probability of acute deterioration vs. number of lab and physiologic values' threshold transgressions within a 72-hour time interval, based on an embodiment reduced to practice.

FIGS. 4A and 4B show the copula regression predicted vs. observed number of lab and physiologic values' threshold transgressions for the N=124 cohort, and the copula regression quantile-quantile plot, indicating satisfactory statistical goodness of fitting, respectively. And, FIG. 5 shows the copula regression for determining the PPOD predicted probability of acute deterioration vs. number of lab and physiologic values' threshold transgressions within a 72-hour time interval, used in this example embodiment reduced to practice.

In one embodiment, a predicted probability of acute deterioration may be used to predict the odds of a crisis within N number of hours. Consider, for example, there is a 50% chance of a crisis in the next 12-72 hours. This information may be used to assign additional observation to particular patients, or if a crisis is judged to be imminent, a call may be initiated to a Rapid Response Team. Another use for the Predicted probability of acute deterioration is to route doctor's rounds, so that walking instructions can be provided for a doctor doing rounds. This may allow a doctor to quickly attend to patients requiring more attention first, and then proceed to patients whose condition is less urgent.

In some embodiments, creating the standard curve may entail reviewing graphs of all previous patients with the same DRG/IDC-10 code in a database and plotting them as one or more curves. The curve may be represented by an average curve, all of the individual patient's curves, a median curve, a top 25th percentile and a bottom 25th percentile, plus or minus some number of standard deviations thereby creating a normative recovery as well as upper and lower bounds, any combination of the foregoing or any other representative indicator as not all embodiments of the present invention are intended to be limited in this respect. By using these types of normative curves a doctor may be able to see that even if a patient is recovering, the patient might be recovering more slowly than the average patient with a similar condition and this slower recovery might be cause for further investigation.

Not only may the grouping codes be useful in comparison with the predicted probability of acute deterioration, but the grouping codes may be utilized in generating a more accurate predicted probability of acute deterioration. In some embodiments, a user may modify the algorithm used to generate the predicted probability of acute deterioration based on the diagnosis or grouping code of the patient in order to have the predicted probability of acute deterioration more accurately reflect the patient's recovery.

Yet another exemplary use of the PPOD arrangement is its use in predicting the length of stay for a patient or group of patients, sometimes termed ELOS (expected length of stay). Such an arrangement may be used to apply to a group of patients and therefore allowing a hospital to create a forward-looking resource plan, i.e. how many nurses are needed on a subsequent day of the week based on the current hospital population in a particular department. Some grouping codes, such as DRG, have ELOS times built into the grouping code, such that someone having a certain surgery will have an ELOS of a certain amount of time.

By comparing a patient's PPOD value with a standard, many inferences may be drawn from the comparison. For example, in some embodiments, patients may be given a category, such as critical, critical but stable, serious, serious but stable, fair, and/or good. These categories may be words or terms, numbers (such as "low risk", "intermediate risk", "high risk", "very high risk" or 1 to 4), colors (such as a heat-map display comprised of red, orange, yellow, and green shading of PPOD values), a system of categorizing, or other appropriate information display system. In addition, the categories may be discrete, such as choosing one of four colors, or they may be continuous.

By having patients categorized, administrative decisions and care priority can be determined accordingly. For example, in some embodiments, a nurse scheduling tool may be incorporated or separately determined which would allow shift nurses to see the conditions of all patients on the floor and assign nurses based on skill level, so that more experienced nurses have more critical patients and newer nurses have more stable patients. In some embodiments, the nurse scheduling tool may rank patients, for example, 1-10 and allocate patients to each nurse so that no nurse has a total patient rank of for example, more than 25 (e.g., two very critical patients of rank 10 and one fair but stable patient of rank 5, four fair but stable patients of ranks 5.2, 5.4, 5.7 and 6.1, or two serious patients of rank 8 and one serious but stable patient of rank 7.2). Similarly, these systems may be applied to routing a doctor's rounds, as described above.

In some embodiments, the PPOD may be used for evaluation purposes. For example, the PPOD may be used to evaluate the performance of a particular doctor's or nurse's performance, or even of the hospital itself. It can also be used to evaluate a particular treatment by studying PPOD charts of patients that underwent a particular treatment.

In addition to evaluation of doctors, the system may be used to compare effectiveness of medical treatments, compare the quality of care provided by different wards or hospitals, and compare the skill of healthcare providers by providing an objective assessment of a patient's health and response to various factors. In some embodiments, the algorithm may be customized after a patient's stay to further evaluate the care of the patient and compare the patient with other patients. For example, if two patients had the same diagnosis and received different treatments, a hospital or doctor may want to compare those two patients' recoveries. Any two patients are evaluated using the same PPOD algorithm, but the comparison is tailored to focus on the recovery from the treatments and exclude unrelated deviations.

In another embodiment, the predicted probability of acute deterioration chart shapes can be clustered to discover the "types" of patient health trajectories. General prototypical trajectories, or trajectories computed as a function of disease or procedure may be compared against actual PPOD charts to determine how a particular patient is responding to treatment. Once a predicted probability of acute deterioration chart is assigned to such a prototypical trajectory, it may further indicate the likelihood of various outcomes. In some embodiments, this may be accomplished by using DRG/ICD-10 groupings.

In another embodiment of the present invention, the PPOD may be used as part of a remote monitoring service, where a remote web-based health service provider can monitor the score of several patients and alert an on-site staff if there is an emergent condition meriting their attention. The PPOD can be calculated using logistic regression equations, neural networks, or other analytical methods. The predicted probability of acute deterioration values may be fed to a cloud-based healthbank or a multi-institution central data hub and be used to monitor for large scale trends in health problems, including a bioterrorism or other public health occurrences.

While in some embodiments an individual predicted probability of acute deterioration falling below a minimum mark or the change in predicted probability of acute deterioration or slope of the time series of predicted probability of acute deterioration values falling below a minimum change may trigger an alarm or be interpreted by a healthcare provider as an indication of the patient's declining physiologic stability, in some embodiments the change in slope or derivative of the slope of the predicted probability of acute deteriorations falling below a certain minimum may trigger an alarm or be interpreted by a healthcare provider as an indication of the patient's rapidly declining health. For example, if a patient is slightly declining and suddenly starts to decline at a much faster rate, this change in the acceleration of the slope may trigger an alarm. In some embodiments, the curvature of the predicted probability of acute deterioration plot may be provided, such as by a presentation and/or comparison module.

Many times a patient's health may be compromised in favor of conforming the patient's care to established pro form a health care best-practices and hospital logistics. For example, many hospitals require their healthcare workers to take a patient's vital signs every 2-4 hours, which requires awakening patients during the nighttime, which interferes with providing full sleep and enter deep sleep, which may be critical to a patient's recovery, and to draw blood from patients every day or two, which can be detrimental to an anemic or hemophiliac. If a patient's course has been so far unremarkable and yet the patient has an increasing predicted probability of acute deterioration, a healthcare worker may rely on the predicted probability of acute deterioration to determine whether or not a contemplated diagnostic test or optional therapeutic procedure may be deferred or omitted in order to allow the patient to better recover.

Some embodiments may include the ability to view a patient's prior hospital visits. In some embodiments, if a patient has a recurring condition, it may be preferable to view that patient's past PPOD values in addition to the present PPOD values, in order to anticipate what trajectories are likely to materialize for this patient in the current acute-care episode. Differences in data source (e.g., HL7 continuity-of-care CCD from a different institution where the patient previously received inpatient care) may be represented with unique point-icons or any other means of differentiating them, as not all embodiments are intended to be limited in these respects. In addition or alternatively, a physician or other provider may click on or hover over a graphed PPOD point to access additional information, such as the data inputted to calculate the PPOD value, or other information.

In some embodiments, the PPOD value or a time series comprised of serial PPOD values may be a medical reference "figure-of-merit" that is used by a health caregiver, such as a physician, nurse or other provider, to track the patient's risk of acute deterioration before, during or after a medical procedure or illness, in order to assist in preventing that patient from reaching a health crisis. When used in this manner, the PPOD display enables the attending physicians and nurses to detect trends in the patient's physiologic stability and hemodynamic compensatory ability over time, particularly in evaluating post-operative recovery in the hospital. It also provides a statistically significant "outcome" for both clinical studies and retrospective studies of the relative efficacies among various surgical procedures or techniques, and among medical treatments and drugs.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A method for automatically modifying a database record associated with a patient based on a probability of acute deterioration for the patient, the method comprising:

communicatively coupling a patient monitoring device with an electronic health record (EHR);

detecting addition of a plurality of serial laboratory measurements or a plurality of serial physiological measurements corresponding to a plurality of measurement variables for the patient to a database maintaining the EHR of the patient, the addition made to the database by the patient monitoring device having a sensor that acquires data from the patient, wherein the EHR includes unstructured data;

responsive to detecting the addition and an indication in the EHR of the patient that the patient is in a facility, calling a first programmatic function that extracts the plurality of serial laboratory measurements and the plurality of serial physiological measurements for the patient from the EHR of the patient;

transforming the plurality of serial laboratory measurements and the plurality of serial physiological measurements to create conditioned patient information by calling a second programmatic function that chronologically orders the plurality of serial laboratory measurements and the plurality of serial physiological measurements using a date-time stamp to construct time series of corresponding addition of each serial laboratory measurement and serial physiological measurement of the plurality of serial laboratory measurements and the plurality of serial physiological measurements;

determining a statistical dependency of a first measurement variable of the plurality of measurement variables on one or more measurement variables of the plurality of measurement variables using a copula regression, wherein the first measurement variable include the time series of transgressions of reference threshold values for laboratory or physical measurements and the one or more measurements variables include the time series of a shock index derived from synchronously measured heart rate and systolic blood pressure;

computing a value representative of a quantity of threshold transgressions in the copula regression of the conditioned patient information;

calculating a predicted probability of acute deterioration by inputting the statistical dependency and the value to a model trained to generate the predicted probability of the acute deterioration based on the input, wherein the predicted probability of acute deterioration represents a forecast probability of current and future acute;

comparing the predicted probability of acute deterioration to a threshold probability;

responsive to the predicted probability of acute deterioration exceeding the threshold probability, initiating undertaking an immunomodulatory treatment.

2. The method of claim 1, wherein the plurality of serial physiological measurements comprise at least one of systolic blood pressure (SBP) measurements, heart rate (HR) measurements, body temperature, or respiratory rate, and wherein the serial laboratory measurements comprise at least one of fibrinogen, ferritin, triglycerides, albumin, leukocytes, platelets, hemoglobin or erythrocytes, serum lactate dehydrogenase (LDH), soluble CD25 (sCD25; interleukin 2 receptor) level for the patient, or spectrum analytic properties of a time series thereof.

3. The method of claim 2, wherein the plurality of serial laboratory measurements and the plurality of serial physiological measurements for the patient are compared to respective threshold values for each measurement type.

4. The method of claim 3, wherein the plurality of physiological measurements comprises a time series of measurements with time series intervals greater than 2 hours.

5. The method of claim 2, further comprising selectively providing a notification to a remote device based on a statistical probability of the acute deterioration.

6. The method of claim 1, wherein a statistical probability of the acute deterioration is determined by logistic regression, K-nearest neighbor clustering, or neural-network, support-vector machine classifier.

7. The method of claim 1, further comprising determining a predicted length of stay for the patient, based at least in part on a statistical probability of the acute deterioration for the patient.

8. The method of claim 1, wherein the transformation further comprises at least one of standard deviation, median absolute deviation, root mean square of successive differences (RMSSD), logarithmic transform of raw values of the one or more measured variables, or power law or Box-Cox transform of the raw values of the one or more measured variables.

9. The method of claim 1, wherein in response to detection that the measure of the acute deterioration or organ system failure for the patient exceeds a threshold, the method further comprises at least one of:

placing a new order in the EHR of the patient;

altering data representative of a care plan of the patient in the EHR of the patient; or modifying a data structure in a database, the modifying including a reservation of resources for the patient in care facility to treat or manage a predicted acute deterioration or the organ system failure.

10. The method of claim 1, further comprising issuing an electronic alert or notification to a care provider or the patient.

11. The method of claim 1, further comprising transmitting a command to a remote server maintaining the EHR of the patient, the command preventing or interrupting discharge orders from being submitted to the EHR of the patient.

12. The method of claim 1, further comprising, responsive to detection that the measure of the acute deterioration or organ system failure for the patient exceeds a threshold, preventing or interrupting a discharge order from being submitted for the patient from the facility until an override has been received.

13. The method of claim 1, wherein in response to detection that the measure of deterioration or organ system failure for the patient exceeds a threshold, the method further comprises altering data representative of a care plan of the patient in the EHR of the patient.

14. The method of claim 1, wherein in response to detection that the measure of the acute deterioration or organ system failure for the patient exceeds a threshold, the method further comprises placing a new order in the EHR of the patient.

15. The method of claim 1, wherein the acute deterioration for the patient is associated with Hemophagocytic lymphohistiocytosis (HLH).

16. The method of claim 1, further comprising, responsive to detection that the measure of the acute deterioration or organ system failure for the patient exceeds a threshold: updating the EHR of the patient to include a representation of a predicted organ system failure.

17. The method of claim 1, further comprising, responsive to detection that the measure of the acute deterioration or organ system failure for the patient exceeds a threshold: automatically modifying the EHR of the patient with a command preventing or interrupting electronic submission of discharge orders to the EHR of the patient until the command is disabled.

18. The method of claim 1, further comprising, responsive to the predicted probability of acute deterioration:

exceeding the threshold probability, assigning a risk category to the patient; and updating, in the EHR, an assignment of nursing resources by allocating the patient to a nurse having a skill level corresponding to the risk category assigned to the patient.

* * * * *